US009248024B2

(12) United States Patent
Ferrari et al.

(10) Patent No.: US 9,248,024 B2
(45) Date of Patent: Feb. 2, 2016

(54) ANKLE PROSTHESIS FOR THE ARTHRODESIS OF THE CALCANEUM

(75) Inventors: Irene Ferrari, Le Touvet (FR); Michael Weber, Aachen (DE)

(73) Assignee: Integra Life Sciences Corporation, Plainsboro, NJ (US)

( * ) Notice: Subject to any disclaimer, the term of this patent is extended or adjusted under 35 U.S.C. 154(b) by 1508 days.

(21) Appl. No.: 11/871,809

(22) Filed: Oct. 12, 2007

(65) Prior Publication Data

US 2008/0195233 A1    Aug. 14, 2008

(30) Foreign Application Priority Data

Oct. 13, 2006    (FR) ...................................... 0609001

(51) Int. Cl.
*A61F 2/42*    (2006.01)
*A61F 2/64*    (2006.01)
*A61F 2/30*    (2006.01)

(52) U.S. Cl.
CPC ....... *A61F 2/4202* (2013.01); *A61F 2002/3055* (2013.01); *A61F 2002/30405* (2013.01); *A61F 2002/30426* (2013.01); *A61F 2002/30604* (2013.01); *A61F 2002/30672* (2013.01); *A61F 2002/30851* (2013.01); *A61F 2002/30884* (2013.01); *A61F 2002/4205* (2013.01); *A61F 2002/4207* (2013.01); *A61F 2002/4212* (2013.01); *A61F 2002/4217* (2013.01); *A61F 2220/0025* (2013.01)

(58) Field of Classification Search
CPC ........... A61F 2/4202; A61F 2002/4212; A61F 2002/4217

USPC ................................................ 623/21.18, 47
See application file for complete search history.

(56) References Cited

U.S. PATENT DOCUMENTS

| 2,393,831 A | 1/1946 | Stader |
| 2,511,051 A | 6/1950 | Dzus |

(Continued)

FOREIGN PATENT DOCUMENTS

| DE | 10123124 | 12/2002 |
| EP | 0864304 | 9/1998 |

(Continued)

OTHER PUBLICATIONS

Bearing. (2011). In Merriam-Webster Online Dictionary. Retrieved Feb. 7, 2011 from http://www.merriam-webster.com/dictionary/bearing?show=0&t=1297115501.*

(Continued)

*Primary Examiner* — Jacqueline Woznicki
(74) *Attorney, Agent, or Firm* — Eva Tan (57) ABSTRACT

A prosthetic ankle assembly including an astragalar component with an upper articular surface that forms part of an ankle joint prosthesis and a lower surface with a shape adapted to engage an upper face of an astragalus. An astragalocalcanean rod is positioned in an astragalocalcanean channel extending from the lower face of the calcaneus to the upper surface of the astragalus. A first end of the astragalocalcanean rod is engage with the lower surface of the astragalar component and a second end of the astragalocalcanean rod is engaged with a lower region of the calcaneus. A distance between the second end of the astragalocalcanean rod is adjustable relative to the lower surface of the astragalar component to adjustably compress the calcaneus against the astragalus.

26 Claims, 4 Drawing Sheets

(56) References Cited

U.S. PATENT DOCUMENTS

| | | | |
|---|---|---|---|
| 3,886,599 A | 6/1975 | Schlein | |
| 3,987,500 A | 10/1976 | Schlein | |
| 4,069,518 A | 1/1978 | Groth, Jr. et al. | |
| 4,175,555 A * | 11/1979 | Herbert | 606/304 |
| 4,232,404 A | 11/1980 | Samuelson et al. | |
| 4,235,428 A | 11/1980 | Davis | |
| 4,257,411 A | 3/1981 | Cho | |
| 4,644,943 A | 2/1987 | Thompson et al. | |
| 4,722,331 A | 2/1988 | Fox | |
| 4,862,882 A | 9/1989 | Venturi et al. | |
| 5,171,289 A | 12/1992 | Tornier | |
| 5,176,682 A | 1/1993 | Chow | |
| 5,217,462 A * | 6/1993 | Asnis et al. | 606/916 |
| 5,236,445 A | 8/1993 | Hayhurst et al. | |
| 5,306,290 A | 4/1994 | Martins et al. | |
| 5,312,409 A | 5/1994 | McLaughlin et al. | |
| 5,314,485 A | 5/1994 | Judet | |
| 5,326,359 A | 7/1994 | Oudard | |
| 5,354,298 A | 10/1994 | Lee et al. | |
| 5,358,526 A | 10/1994 | Tornier | |
| 5,380,334 A | 1/1995 | Torrie et al. | |
| 5,383,937 A | 1/1995 | Mikhail | |
| 5,403,321 A | 4/1995 | DiMarco | |
| 5,405,399 A | 4/1995 | Tornier | |
| 5,423,860 A | 6/1995 | Lizardi et al. | |
| 5,429,639 A | 7/1995 | Judet | |
| 5,458,650 A | 10/1995 | Carret et al. | |
| 5,464,427 A | 11/1995 | Curtis et al. | |
| 5,480,403 A | 1/1996 | Lee et al. | |
| 5,486,197 A | 1/1996 | Le et al. | |
| 5,505,731 A | 4/1996 | Tornier | |
| 5,545,228 A * | 8/1996 | Kambin | 606/60 |
| 5,591,168 A | 1/1997 | Judet et al. | |
| 5,662,651 A | 9/1997 | Tornier et al. | |
| 5,674,224 A | 10/1997 | Howell et al. | |
| 5,676,702 A | 10/1997 | Ratron | |
| 5,690,676 A | 11/1997 | DiPoto et al. | |
| 5,702,447 A | 12/1997 | Walch et al. | |
| 5,702,457 A | 12/1997 | Walch et al. | |
| 5,702,478 A | 12/1997 | Tornier | |
| 5,766,256 A | 6/1998 | Oudard et al. | |
| 5,766,259 A | 6/1998 | Sammarco | |
| 5,824,106 A | 10/1998 | Fournol | |
| 5,827,285 A | 10/1998 | Bramlet | |
| 5,827,289 A | 10/1998 | Reiley et al. | |
| 5,879,395 A | 3/1999 | Tornier et al. | |
| 5,931,837 A | 8/1999 | Marsh et al. | |
| 6,053,920 A * | 4/2000 | Carlsson et al. | 606/304 |
| 6,086,591 A | 7/2000 | Bojarski | |
| 6,136,032 A * | 10/2000 | Viladot Perice et al. | 623/21.18 |
| 6,162,254 A | 12/2000 | Timoteo | |
| 6,165,224 A | 12/2000 | Tornier | |
| 6,168,629 B1 | 1/2001 | Timoteo | |
| 6,168,631 B1 | 1/2001 | Maxwell et al. | |
| 6,171,341 B1 | 1/2001 | Boileau et al. | |
| 6,183,519 B1 * | 2/2001 | Bonnin et al. | 623/21.18 |
| 6,203,575 B1 | 3/2001 | Farey | |
| 6,206,925 B1 | 3/2001 | Tornier | |
| 6,299,646 B1 | 10/2001 | Chambat et al. | |
| 6,328,758 B1 | 12/2001 | Tornier et al. | |
| 6,334,874 B1 | 1/2002 | Tornier et al. | |
| 6,379,387 B1 | 4/2002 | Tornier | |
| 6,409,767 B1 | 6/2002 | Perice et al. | |
| 6,413,260 B1 | 7/2002 | Berrevoets et al. | |
| 6,454,809 B1 | 9/2002 | Tornier | |
| 6,458,134 B1 | 10/2002 | Songer et al. | |
| 6,488,712 B1 | 12/2002 | Tornier et al. | |
| 6,508,841 B2 * | 1/2003 | Martin et al. | 623/23.12 |
| 6,517,543 B1 | 2/2003 | Berrevoets et al. | |
| 6,540,770 B1 | 4/2003 | Tornier et al. | |
| 6,579,293 B1 * | 6/2003 | Chandran | 606/64 |
| 6,582,469 B1 | 6/2003 | Tornier | |
| 6,599,295 B1 | 7/2003 | Tornier et al. | |
| 6,616,694 B1 | 9/2003 | Hart | |
| 6,626,946 B1 | 9/2003 | Walch et al. | |
| 6,648,890 B2 | 11/2003 | Culbert et al. | |
| 6,663,669 B1 * | 12/2003 | Reiley | 623/21.18 |
| 6,673,116 B2 | 1/2004 | Reiley | |
| 6,685,706 B2 | 2/2004 | Padget et al. | |
| 6,761,740 B2 | 7/2004 | Tornier | |
| 6,767,368 B2 | 7/2004 | Tornier | |
| 6,802,864 B2 | 10/2004 | Tornier | |
| 6,824,567 B2 | 11/2004 | Tornier et al. | |
| 6,860,902 B2 * | 3/2005 | Reiley | 623/21.18 |
| 6,875,236 B2 * | 4/2005 | Reiley | 623/21.18 |
| 6,890,357 B2 | 5/2005 | Tornier | |
| 6,926,739 B1 * | 8/2005 | O'Connor et al. | 623/21.18 |
| 6,969,406 B2 | 11/2005 | Tornier | |
| 7,025,790 B2 | 4/2006 | Parks et al. | |
| 7,033,396 B2 | 4/2006 | Tornier | |
| 7,033,398 B2 * | 4/2006 | Graham | 623/21.18 |
| 7,314,488 B2 | 1/2008 | Reiley | |
| 8,048,164 B2 * | 11/2011 | Reiley | 623/21.18 |
| 2003/0009170 A1 | 1/2003 | Tornier | |
| 2003/0009171 A1 | 1/2003 | Tornier | |
| 2003/0028198 A1 | 2/2003 | Tornier et al. | |
| 2004/0030399 A1 | 2/2004 | Asencio | |
| 2004/0134821 A1 | 7/2004 | Tornier | |
| 2004/0210220 A1 | 10/2004 | Tornier | |
| 2004/0215200 A1 | 10/2004 | Tornier | |
| 2004/0230197 A1 | 11/2004 | Tornier et al. | |
| 2005/0049709 A1 | 3/2005 | Tornier | |
| 2005/0055102 A1 | 3/2005 | Tornier et al. | |
| 2005/0107791 A1 | 5/2005 | Manderson | |
| 2005/0124995 A1 | 6/2005 | Reiley | |
| 2005/0165490 A1 | 7/2005 | Tornier | |
| 2005/0177243 A1 | 8/2005 | Lepow et al. | |
| 2005/0203536 A1 | 9/2005 | Laffargue et al. | |
| 2005/0278030 A1 | 12/2005 | Tornier et al. | |
| 2005/0278031 A1 | 12/2005 | Tornier et al. | |
| 2005/0278032 A1 | 12/2005 | Tornier et al. | |
| 2005/0278033 A1 | 12/2005 | Tornier et al. | |
| 2005/0288791 A1 | 12/2005 | Tornier et al. | |
| 2005/0288792 A1 | 12/2005 | Landes et al. | |
| 2006/0015105 A1 * | 1/2006 | Warren et al. | 606/72 |
| 2006/0015185 A1 | 1/2006 | Chambat et al. | |
| 2006/0173457 A1 | 8/2006 | Tornier | |
| 2006/0235538 A1 | 10/2006 | Rochetin et al. | |
| 2007/0043265 A1 | 2/2007 | Rochetin | |
| 2007/0129808 A1 * | 6/2007 | Justin et al. | 623/20.15 |
| 2007/0162025 A1 | 7/2007 | Tornier et al. | |
| 2007/0173947 A1 | 7/2007 | Ratron et al. | |
| 2007/0179628 A1 | 8/2007 | Rochetin | |
| 2007/0288097 A1 * | 12/2007 | Hurowitz | 623/47 |
| 2009/0082875 A1 * | 3/2009 | Long | 623/21.18 |
| 2010/0010490 A1 * | 1/2010 | Brigido | 606/64 |
| 2011/0054473 A1 * | 3/2011 | Brigido | 606/62 |
| 2012/0165701 A1 * | 6/2012 | Manderson | 600/587 |
| 2015/0057665 A1 * | 2/2015 | Neal et al. | 606/87 |

FOREIGN PATENT DOCUMENTS

| | | |
|---|---|---|
| FR | 2220235 | 10/1974 |
| FR | 2700462 | 7/1994 |
| FR | 2759900 | 8/1998 |
| WO | WO 92/15257 | 9/1992 |
| WO | 0069373 | 11/2000 |
| WO | 0130264 | 5/2001 |
| WO | WO 01/30264 | 5/2001 |
| WO | 0189427 | 11/2001 |

OTHER PUBLICATIONS

Ring. (2011). In Merriam-Webster Online Dictionary. Retrieved Feb. 7, 2011 from http://www.merriam-webster.com/dictionary/ring.*

International Search Report from French application No. 0609001 dated May 14, 2007.

Internationa Search Report from French application No. 0609001 dated May 14, 2007.

Rochetin et al., U.S. Appl. No. 11/401,415, entitled "Surgical Apparatus for Implantation of a Partial or Total Knee Prosthesis," filed Apr. 11, 2006.

* cited by examiner

ANKLE PROSTHESIS FOR THE ARTHRODESIS OF THE CALCANEUM

CROSS-REFERENCE TO RELATED APPLICATIONS

The present application claims priority to prior French Application No. 06 09001, filed Oct. 13, 2006, entitled ANKLE PROSTHESIS FOR THE ARTHRODESIS OF THE CALCANEUM.

FIELD OF THE INVENTION

The present invention relates to a prosthetic ankle assembly and to a surgical method for implanting such an assembly, and in particular, to the treatment of an ankle in which the articulation between the astragalus and the calcaneus are damaged.

BACKGROUND OF THE INVENTION

One possible treatment involves fusing the three bones represented by the calcaneus, astragalus and tibia, as is proposed in US-A-2005/0107791. A long compression screw internally connects the tibia and the calcaneus by passing through the astragalus, in such a way as to block these three bones relative to one another. This results in a considerable loss of mobility for the patient, since the ankle is totally blocked.

Another possible treatment involves fusing the calcaneus and astragalus, with the aid of a dedicated arthrodesis rod and re-establishing the articular capacity between the astragalus and tibia, by implanting an ankle joint prosthesis. However, the two articulations then have to be treated in two stages: the arthrodesis of the calcaneus and astragalus requires a consolidation period of at least six months, which delays the implantation of the articular prosthesis between the astragalus and the tibia.

US-A-2005/0288792 discloses an astragalar component of an ankle joint prosthesis with which it is possible to re-establish the articular capacity between the astragalus and the tibia, while at the same time using an astragalocalcanean rod that extends from a lower side of the astragalar component to the upper part of the calcaneus, in so doing passing right through the astragalus. In one embodiment, the upper end of this rod is screwed directly into internal threads of the astragalar component, which threads open out on the lower side of this component. Before being implanted, the component and the rod are firmly immobilized relative to each other by screwing. When this screwed assembly is implanted, the rod guarantees good anchoring of the astragalar component, since the latter is thus fixed both to the astragalus and also to the upper part of the calcaneus, which explains why the prosthetic assembly is more specifically intended for revision of an arthroplasty of the ankle. However, the assembly does not effectively block the articulation between the calcaneus and the astragalus, since relative movements around and/or along the rod remain possible and, in practice, appear quickly.

FR-A-2 220 235 proposes a prosthetic ankle assembly comprising an astragalar component of an ankle joint prosthesis in the form of a support designed to be fixed to the astragalus of a patient. This support is intended to cooperate in an articulated manner with a tibial rod, with interposition of an intermediate articulated component. In its lower part, the astragalar support is joined to three anchoring feet, namely two anterior feet and one posterior foot, which are intended respectively to be inserted into corresponding cavities formed in the astragalus and in the calcaneus. As regards the posterior foot, one embodiment entails this foot being formed by at least one sagittal screw that passes through the support from top to bottom, until bearing with its head on the support, while its stem is inserted, without being screwed, into the cavity of the calcaneus, plugged with cement. The benefit of using such a screw is that, if necessary, it can be unscrewed in order to facilitate the removal of the support. Thus, the posterior foot of this prosthetic assembly provides a stable means of bearing on the calcaneus, but, even in the form of a screw inserted into cement, this foot does not totally block the articulation between the astragalus and the calcaneus in an effective manner.

WO-A-01/30264 and US-A-2005/124995 for their part disclose a prosthetic ankle assembly comprising an astragalocalcanean rod that is introduced into a cavity formed beforehand through the astragalus and in the upper part of the calcaneus. This rod is used to anchor an astragalar plate, which is fitted in place and fixed to the astragalocalcanean rod after the rod has been placed in the aforementioned bone cavity. Hence, this rod does not provide any effective blocking of the articulation between the calcaneus and the astragalus so that, in order to limit the relative movements between these two bones, additional screws are fitted between the astragalar plate and the astragalocalcanean rod, in order to stabilize the position of the latter.

BRIEF SUMMARY OF THE INVENTION

The present invention is directed to a method and apparatus that blocks the articulation between the calcaneus and the astragalus and to re-establish an articular capacity between the astragalus and the tibia of a patient, all in a single intervention.

To this end, the subject matter of the invention is a prosthetic ankle assembly, comprising an astragalar component which forms part of an ankle joint prosthesis and which is designed to be fixed to the astragalus of a patient. An astragalocalcanean rod of which a first longitudinal end is designed to be fixed to the astragalar component, by its shape complementing that of a dedicated part of the astragalar component. The dedicated part is provided on a lower side of this component intended to be directed towards an upper face of the astragalus. The astragalocalcanean rod is equipped, at its second longitudinal end, with an engagement feature for osseous engagement of the calcaneus of the patient, so as to approximate and thereby compress the calcaneus against the astragalus when the first end of the rod is fixed to the dedicated part of the astragalar component.

When the prosthetic assembly according to the invention is implanted, its astragalar component permits articular movements between the astragalus and the tibia of a patient, especially by being connected to a prosthetic tibial component fixed to the tibia, and to a prosthetic bearing interposed between the astragalar and tibial components. On the other hand, the astragalocalcanean rod blocks the articulation between the calcaneus and the astragalus, by these two bones being compressed against each other. In practice, this bone compression is obtained by fixing the first end of the rod in the astragalar component, which engages the second end of the rod directly with the calcaneus. For this purpose, a fixation means and the engagement means provided respectively at the ends of the rod are structurally configured to obtain a progressive compression effect between the calcaneus and the astragalus as the second end of the rod advances into the calcaneus, whilst the first end is coupled to the dedicated part of the astragalar component resting on the astragalus.

In practice, the rod is introduced from a lower face of the calcaneus into an astragalocalcanean channel that has been drilled beforehand through the calcaneus and the astragalus and that opens out on the dedicated part of the astragalar component when the latter is placed on an upper face of the astragalus. Thus, advantageously in a single surgical intervention, the astragalar component and the astragalocalcanean rod are implanted by being coupled to each other during the intervention, while the rod passes right through the calcaneus and the astragalus, in order to compress them and thereby immobilize them against each other. In other words, the operation of arthroplasty between the astragalus and the tibia and the operation of arthrodesis between the astragalus and the calcaneus are performed during the same surgical intervention, which limits the surgical risks faced by the patient and which allows the surgeon to use the same surgical routes for the two operations.

In addition, the astragalocalcanean rod ensures immobilization of the astragalar component relative to the astragalus and to the calcaneus, which improves the fit of the astragalar component. Moreover, in the event of revision of the prosthetic assembly according to the invention, the bearing action on the calcaneus is safe and reliable in the sense that this bone is firmly fused to the astragalus.

According to other advantageous characteristics of this prosthetic ankle assembly, taken either singly or in all the technically possible combinations:

- the astragalocalcanean rod is designed to extend in length from the upper face of the astragalus, on which the astragalar component is fixed, as far as a lower face of the calcaneus directed away from the astragalus;
- the engagement means comprises an external thread designed to engage in the bone substance of the calcaneus when the first end of the astragalocalcanean rod is fixed in the dedicated part of the astragalar component;
- the engagement means comprises a ring, fixedly or moveably surrounding the second end of the astragalocalcanean rod and adapted to be pressed against a lower face of the calcaneus, opposite to the astragalus, when the first end of the rod is fixed to the dedicated part of the astragalar component;
- the engagement means for engaging the calcaneus has a maximum transverse dimension strictly greater than the maximum transverse dimension of a fixation means for fixing the first end of the astragalocalcanean rod to the astragalar component;
- either the first end of the astragalocalcanean rod or the dedicated part of the astragalar component is equipped with an external thread, while the other of them forms a substantially complementary internal thread;
- the astragalar component is equipped, on its lower side, with an anchoring means for osseous anchoring in the astragalus, inside of which anchoring means the dedicated part is arranged;
- the anchoring means includes a hollow stub in which the external thread or internal thread of the astragalar component is delimited, preferably in a manner substantially coaxial to the rest of the stub;
- the astragalocalcanean rod is equipped, at its second longitudinal end, with a driving profile, preferably driven in rotation on itself, designed to cooperate with a tool for coupling the rod to the astragalar component;
- the profile or another profile for driving the rod is designed to cooperate with a tool for disconnection between the rod and the astragalar component;
- the assembly also comprises a tibial component of an ankle joint prosthesis, designed to be fixed to the tibia of the patient, and a prosthetic bearing designed to be interposed between the astragalar component and tibial component.

The invention also relates to a surgical method for implanting a prosthetic ankle assembly, the assembly comprising an astragalar component of an ankle joint prosthesis, and an astragalocalcanean rod of which a first of its two longitudinal ends is designed to be fixed to the astragalar component, by its shape complementing that of a dedicated part of the component, and of which the second longitudinal end is equipped with an engagement means of osseous engagement. The method of implantation comprising steps of:

preparing an upper face of an astragalus to receive an astragalar component;

forming an astragalocalcanean channel between an the upper face of the astragalus and a lower face of a calcaneus;

locating the astragalar component on the upper face of the astragalus;

inserting an astragalocalcanean rod into the astragalocalcanean channel from the lower face of the calcaneus;

engaging a first end of the astragalo-calanean rod with the astragalar component and a second end of the astragalocalanean rod with a lower region of the calcaneus; and adjusting a distance between the second end of the astragalocalcanean rod relative to a lower surface of the astragalar component to adjustably compresses the calcaneus against the astragalus.

This method makes it possible, in a single surgical intervention, to implant a prosthetic ankle assembly of the kind defined above, in order to permit arthrodesis of the calcaneus and astragalus and, at the same time, arthroplasty between the astragalus and the tibia of a patient. Arthrodesis refers to a surgical fixation of a joint, ultimately resulting in bone fusion. Basically, the procedure is artificially induced ankylosis performed to relieve pain or provide support in a diseased or injured joint.

According to an advantageous embodiment of this method, during step i), a substantially cylindrical recess is hollowed out in the upper face of the astragalus in order to receive a hollow bone-anchoring stub which is provided on the astragalar component and in which the dedicated part is arranged, and, during step ii), the astragalocalcanean channel is drilled from the upper face of the astragalus, in a continuation of the recess.

In this case, to make matters easier, a drill bushing is used to drill the astragalocalcanean channel, by resting this bushing in the recess formed during step i).

Advantageously, in order to promote the fusion of the calcaneus and the astragalus, the method comprises, before step ii), an additional surgical step during which bone substance is inserted between the astragalus and the calcaneus by arthroscopy.

Moreover, after consolidation of the arthrodesis of the calcaneus and astragalus, the method advantageously comprises a postoperative step in which the astragalocalcanean rod is withdrawn by disconnecting its first end from the dedicated part of the astragalar component.

BRIEF DESCRIPTIONS OF THE SEVERAL VIEWS OF THE DRAWING

The invention can be better understood on reading the following description given purely by way of example and made with reference to the drawings, in which.

DETAILED DESCRIPTION OF THE INVENTION

Figure 1:
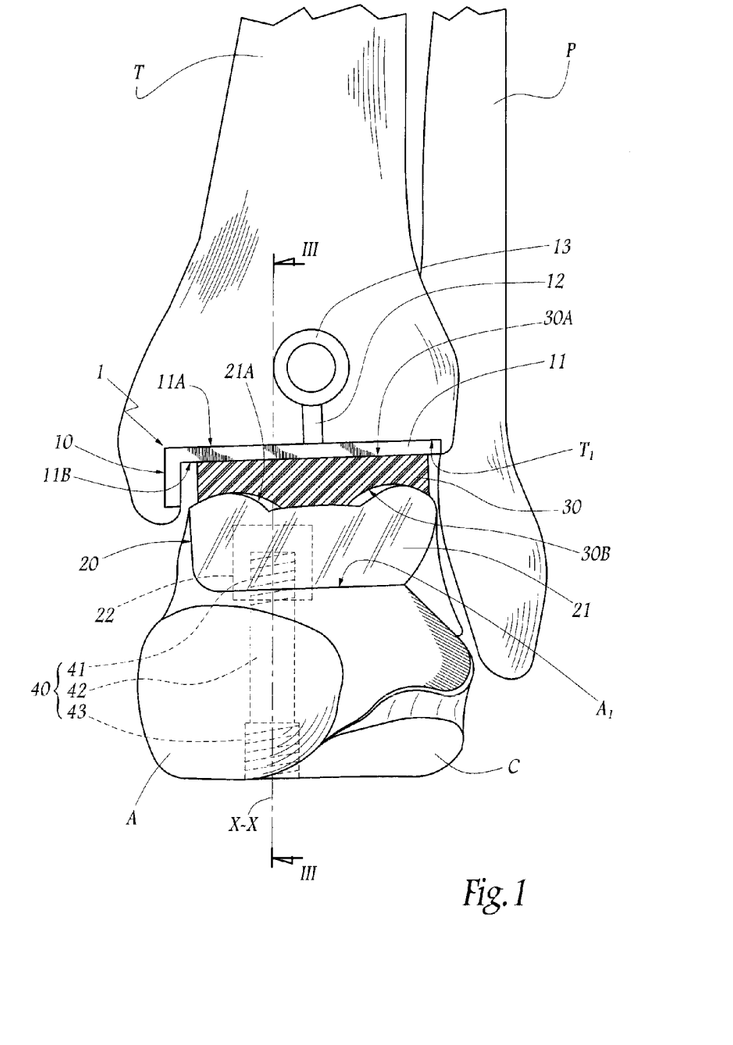
FIG. 1 is a front view, in partial cross section, of a prosthetic ankle assembly implanted in the left ankle of a patient in accordance with an embodiment of the present invention.

FIG. 1 shows schematically the lower ends of a tibia T and of a peroneal bone P or fibula of a human being, and also the corresponding astragalus A and calcaneus C, thereby illustrating the constituent bones of the left ankle of a patient. FIG. 1 also shows a prosthetic ankle assembly 1 comprising four separate components implanted in the ankle of the patient, namely a tibial component 10, an astragalar component 20, a prosthetic bearing 30, interposed between the tibial and astragalar components, and an astragalocalcanean rod 40. In FIG. 1, only the bearing 30 is shown in frontal section, whereas the broken lines are used to symbolize the contours of the components concealed by bone substance.

For convenience, the description that follows relates to the bones of the ankle in their anatomical position, that is to say the terms "posterior" or "rear", "anterior" or "front", "upper", "lower", etc., are to be understood in relation to the ankle of the patient when standing upright on a substantially horizontal surface.

The tibial component 10 comprises a plate 11 which is attached in a fixed manner to the lower end of the tibia T. For this purpose, the plate 11, on its upper face 11A, is joined, via a sagittal fin 12, to a hollow bone-anchoring stub 13. Additional and/or alternative means for anchoring the plate 11 are conceivable, provided that they effectively immobilize the tibial component at the lower end of the tibia T.

On its lower side, the plate 11 delimits a plane surface 11B intended to form a sliding support for the plane upper surface 30A of the bearing 30.

The astragalar component 20 comprises a main block 21 attached in a fixed manner to the upper end of the astragalus A. For this purpose, the block 21 is made integral with a hollow bone-anchoring stub 22 that extends downwards from the lower side 21B of the block 21, as is represented by broken lines in FIG. 1 and as can be clearly seen in FIG. 2.

Figure 2:
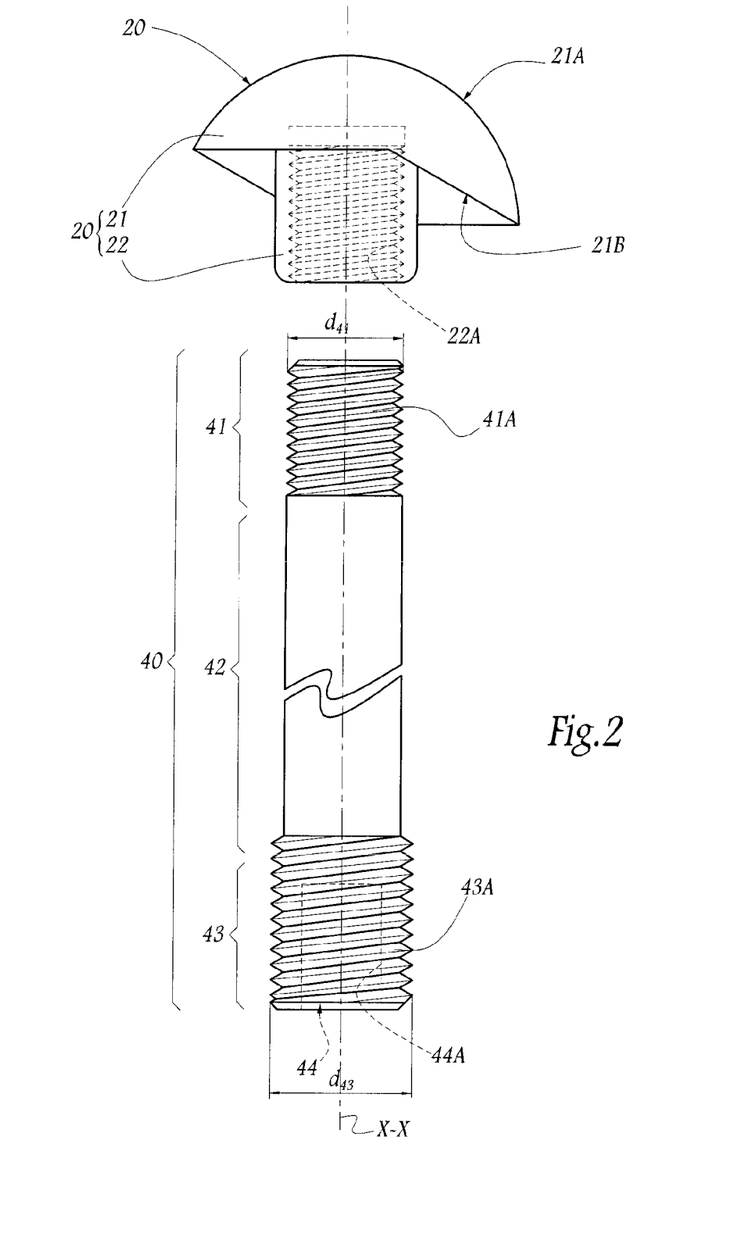
FIG. 2 is an exploded side view, according to the arrow II indicated in FIG. 1, of part of the prosthetic assembly, depicted without the bones of the ankle.

On its upper side, the block 21 delimits an articular surface 21A intended to cooperate with a matching articular surface 30B delimited by the lower side of the bearing 30. In sagittal section, the surface 21A has an arched profile, with its concavity directed downwards, as can be seen in FIG. 2. The articular surfaces 21A and 30B are thus designed to slide against each other along this curved profile, in what is an essentially antero-posterior direction. Advantageously, these surfaces 21A and 30B between them permit a medio-lateral clearance, which combines with the curved movement of sliding in the antero-posterior direction.

As is shown in FIG. 2, the rod 40 extends lengthwise about a completely vertical central axis X-X. This rod comprises, in succession along its length, a first threaded end 41, an externally smooth and regular part 42, and a second threaded end 43. The end 41, the regular part 42 and the end 43 are successively of increasing size, such that, on the one hand, the maximum diameter $d_{41}$ of the external thread 41A of the end 41, that is to say the maximum transverse dimension of this end 41 in the area of the crest of the thread, is less than or equal to the external diameter of the part 42, and, on the other hand, the maximum diameter $d_{43}$ of the external thread 43A of the end 43, that is to say the maximum transverse dimension of this end 43 at the crest of the thread 43A, is strictly greater than the diameter of the regular part 42.

The external thread 41A of the end 41 is designed to be received by screwing into a complementary internal thread 22A which, as is indicated by broken lines in FIG. 2, is delimited by the inner face of the hollow stub 22 and is preferably centred on the central longitudinal axis of this stub.

At its end 43, the rod 40 delimits a recess 44 which is substantially centred on the axis X-X and opens out axially downwards to the outside, as is indicated by broken lines in FIG. 2. This recess 44 has a transverse profile 44A, for example of square shape, intended to cooperate with a complementary tool for driving the rod 40 in rotation on itself about the axis X-X.

A surgical method for implanting the prosthetic ankle assembly 1 will now be described.

Figure 3A:
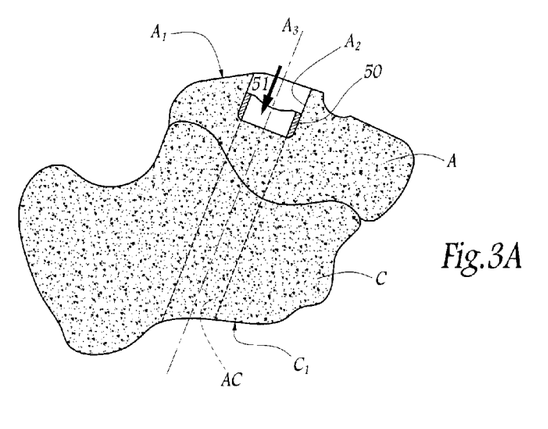
FIGS. 3A and 3B are schematic cross sections, along the line III-IIi in FIG. 1, illustrating two successive steps in the implantation of the prosthetic assembly.

In a first step, the bones of the patient's ankle have to be prepared. For this purpose, the surgeon uses cutting means (not shown) in such a way as to, on the one hand, resect the lower end of the tibia T and form a substantially plane surface $T_1$, and, on the other hand, resect the upper end of the astragalus A and form a multi-facet surface $A_1$ comprising two main surfaces which are inclined relative to each other, as can be seen in FIG. 3A. In the face $A_1$, a cylindrical recess $A_2$, indicated by broken lines in FIG. 3A, is hollowed out in an overall vertical direction, for example by means of a milling cutter. This recess $A_2$ thus defines a central longitudinal axis $A_3$.

At this stage of the surgical intervention, the upper face $A_1$ of the astragalus A is in a configuration suitable for receiving the astragalar component 20, it being understood that the recess $A_2$ is made substantially complementary to the stub 22 in order to anchor this component 20 on the astragalus. However, before fitting the astragalar component 20 in place, the surgeon drills through the astragalus A and calcaneus C, from the upper face $A_1$ of the astragalus to a lower face $C_1$ of the calcaneus, in such a way as to form an astragalocalcanean channel AC indicated by broken lines in FIG. 3A. This channel AC is drilled in a rectilinear continuation of the recess $A_2$, by being substantially centred on the axis $A_3$. To do this, the surgeon advantageously uses a drill bushing 50, indicated partially and schematically in FIG. 3A. This bushing 50 has a tubular shape designed to be received in a substantially complementary manner in the recess $A_2$, substantially coaxial to the recess. In this way, the bushing 50 bears in the recess $A_2$ in such a way as to guide the introduction and advance of a drill bit successively through the astragalus and the calcaneus, as is indicated by the arrow 51 in FIG. 3A. The surgeon thus drills the astragalocalcanean channel AC rapidly and with precision, using ancillary equipment traditional in the field of orthopaedic surgery.

Figure 3B:
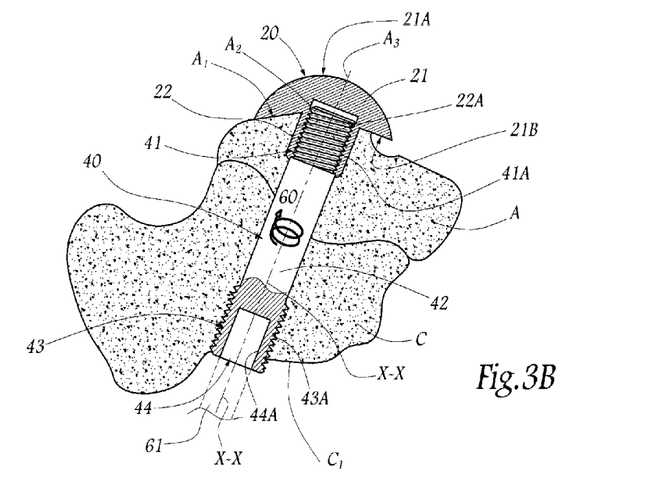

After the astragalocalcanean channel AC has been drilled, the surgeon places the astragalar component 20 on the upper face $A_1$ of the astragalus A and places the astragalocalcanean rod 40 in the channel AC. More precisely, the rod 40 is introduced into the channel AC from the lower face $C_1$ of the calcaneus, with its end 41 directed upwards. The internal diameter of the channel AC is made substantially equal to the external diameter of the regular part 42, such that the rod is easily advanced through the channel in an upward translational movement and parallel to the axis $A_3$, until the end 41 reaches the point where the channel AC opens into the recess $A_2$. As this recess is occupied by the stub 22, advancing the rod 40 requires the latter to be driven in rotation on itself about the axis X-X, in such a way as to screw the external thread 41A into the internal thread 22A, as is indicated by the arrow 60. In practice, the rod is driven in rotation by means of a tool whose head, indicated only by broken lines and reference number 61 in FIG. 3B, is engaged with the profile 44A in the recess 44.

It will be understood that, by giving the rod 40 a suitable lengthwise dimension, the screwing of the end 41 into the stub 22 is accompanied by the screwing of the end 43 into the calcaneus, the external thread 43A engaging directly in the bone substance of the calcaneus at the point where the channel AC opens out on the lower face $C_1$ of the calcaneus. In other words, the rod 40 has a length substantially equal to that of the astragalocalcanean channel AC, such that the rod can extend through the astragalus and the calcaneus with its end 41 in the area of the upper face $A_1$ of the astragalus and with its end 43 in the area of the lower face $C_1$ of the calcaneus.

The twin screwing of the external threads 41A and 43A causes the astragalus A and the calcaneus C to be gradually approximated to each other, thereby compressing these two bones against each other in the area of their respective contacting surfaces. It will be appreciated that the structural features of these external threads, in particular their respective pitch, are chosen so as to achieve compression values that are sufficient to efficiently block the astragalus and the calcaneus against each other, without generating excessive stress in the bones.

The other components of the prosthetic assembly 1 are implanted in parallel with this. The tibial component 10 is attached and immobilized on the lower end of the tibia T, with its plate 11 resting flat against the face $T_1$, then the prosthetic bearing 30 is attached between the components 10 and 20. The assembly 1 is then in the implantation configuration illustrated in FIG. 1 and the surgical intervention is concluded.

After consolidation of the arthrodesis between the astragalus A and the calcaneus C, which generally takes between six and twelve months, the astragalocalcanean rod 40 can be withdrawn by unscrewing its ends 41 and 43. The surgeon then advantageously uses the profile 44A by introducing a suitable disconnecting tool into the latter. To promote and accelerate this arthrodesis, bone substance can advantageously be inserted between the astragalus and the calcaneus before implantation of the prosthetic assembly 1. Before jointly drilling right through the astragalus A and the calcaneus C, an arthroscope is inserted into the junction area between the astragalus and the calcaneus in order to place bone substance there.

Figure 4:
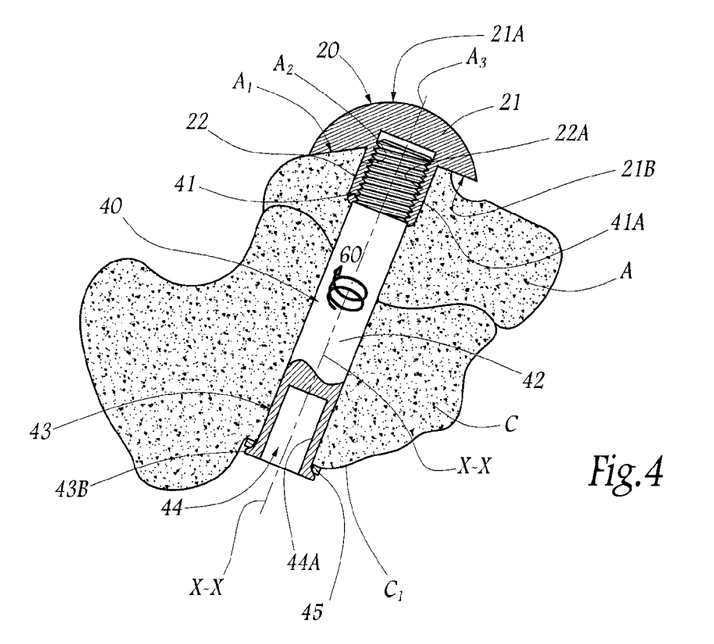
FIG. 4 is a view similar to FIG. 3B, illustrating a variant of the prosthetic ankle assembly in accordance with an embodiment of the present invention.

FIG. 4 shows a variant of the astragalocalcanean rod 40, which differs from the embodiment considered in FIGS. 1 to 3B only at its lower end 43. The external thread 43A is cancelled, so that the external surface of the end 43 is smooth and extends in the straight continuation of the external surface of the regular part 42, except at its end area that forms a bulge 43B radially protruding externally from the rest of this surface. Unlike the embodiment of FIGS. 1 to 3B, the end 43 of the rod 40 of FIG. 4 is associated with a ring 45 externally surrounding this end. This ring has an internal diameter that is both substantially equal or greater than the external diameter of end 43, except at its end bulge 43B, and lower than the maximum external diameter of this bulge. In practice, the ring 45 is pulled around the rod 40 by being introduced from upper end 41 while the rod is still not introduced into the astragalocalcanean channel AC.

When the external thread 41A of the end 41 of the rod 40 is screwed into internal thread 22A of the astragalar component 20, by driving in rotation the rod by means of the tool whose head is engaged within the recess 44, the ring 45 is thus interposed between the lower face $C_1$ of the calcaneus C and the end bulge 43B of the rod until this bulge drives the ring 45 in a pressed contact against the face $C_1$ of the calcaneus. Thus, the ring 45 transmits and distributes the clamping stress on the face $C_1$ of the calcaneus, in the same way as a washer. The calcaneus is thus compressed against the astragalus A, until to efficiently block the astragalus and the calcaneus against each other.

A radial clearance between the internal face of the ring 45 and the external face of the end 43, above its end bulge 43B, allows adjustment of the position of the ring with respect to the rod during its pressing against the calcaneus C. Thus, this relative mobility between the ring and the end 43 compensates for a potential misalignment between the central axis of the ring and the axis X-X of the rod.

According to a not shown variant, the ring 45 is fixedly secured at the lower end 43 of the rod 40, for example being directly integral with the rod. In this case, in order to increase the pressing surface of this fixed ring against the lower face $C_1$ of the calcaneus C during the screwing of the external thread 41A into the astragalar component 20, this calcanean face $C_1$ is, if necessary, beforehand wrought, so that a substantially plane surface, inscribed in a plane substantially perpendicular to the axis $A_3$ of the astragalocalcanean channel AC, is delimitated around the point where this channel opens into the recess $A_2$.

Configurations other than the external thread 43A and the ring 45 can be provided at the lower end 43 of the astragalocalcanean rod 40 in order to engage the calcaneus C and compress it against the astragalus A when screwing the upper end 41 into the astragalar component 20. For example, the lower end 43 can have an outer surface in the shape of a truncated cone or flare widening towards the bottom.

Other variations on the prosthetic ankle assembly 1 and on the implantation method that have been described above are also conceivable. By way of example:

The central axis of the internal thread 22A can be offset from the central axis of the stub 22, the drill bushing 50 then being provided with a similar offset in order to drill the astragalocalcanean channel AC in the possibly inclined continuation of the recess $A_2$;

The structure of internal thread 22A and external thread 41A can be reversed, such that the end 41 of the rod 40 forms an internal thread that can be screwed around an external thread formed in the stub 22, for example delimited by a central pin internal to this stub; more generally, other types of means permitting coupling through complementary shapes between the upper end of the rod 40 and the lower side 21B of the astragalar component 20 are conceivable, provided that these means lead to engagement of the lower end of the rod with the calcaneus C in order to compress the latter against the astragalus A; thus, a coupling by means of a bayonet structure is possible, and also coupling structures with stressing obtained exclusively through rectilinear translation;

By virtue of the fact that they bear slidingly on each other at their surfaces 11A and 30A, the tibial component 10 and the bearing 30 are movable relative to each other, which generally leads the ankle prosthesis comprising the elements 10, 20 and 30 to be designated as a prosthesis with a "movable bearing"; however, the astragalar component 20 can alternatively be joined to a "fixed" bearing, that is to say a bearing placed fixedly against a tibial component;

The astragalar component 20 and the astragalocalcanean rod 40 are not necessarily to be used jointly with a tibial component and a prosthetic bearing such as the elements 10 and 30; the astragalar component can in fact be made to cooperate in an articulated manner directly with the lower anatomical end of the tibia T if the latter has sufficient articular capacity; the prosthetic ankle assembly can then be designated as a partial prosthetic assembly, whereas the prosthetic assembly 1 in FIG. 1 is to be considered as a total prosthetic assembly; and/or If necessary, the fixation of the astragalar component 20 to the astragalus A can be strengthened by additional means.

Patents and patent applications disclosed herein, including those cited in the Background of the Invention, are hereby incorporated by reference. Other embodiments of the invention are possible. It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

In practice, the rod is introduced from a lower face of the calcaneus into an astragalocalcanean channel that has been drilled beforehand through the calcaneus and the astragalus and that opens out on the dedicated part of the astragalar component when the latter is placed on an upper face of the astragalus. Thus, advantageously in a single surgical intervention, the astragalar component and the astragalocalcanean rod are implanted by being coupled to each other during the intervention, while the rod passes right through the calcaneus and the astragalus, in order to compress them and thereby immobilize them against each other. In other words, the operation of arthroplasty between the astragalus and the tibia and the operation of arthrodesis between the astragalus and the calcaneus are performed during the same surgical intervention, which limits the surgical risks faced by the patient and which allows the surgeon to use the same surgical routes for the two operations.

What is claimed is:

1. A prosthetic ankle assembly comprising:
   an astragalar component comprising an upper articular surface that forms part of an ankle joint prosthesis and a lower surface comprising a shape adapted to engage an upper face of an astragalus; and
   an astragalocalcanean rod sized to be positioned in a bore extending completely through the astragalus and a calcaneus of an ankle, the astragalocalcanean rod comprising a first end, which is adapted to couple to the lower surface of the astragalar component, and a second end adapted to engage with a lower surface of the calcaneus, such that during implantation, the astragalocalcanean rod is configured to be inserted through a lower face of the calcaneus so that the first end of the astragalocalcanean rod is coupled to the lower surface of the astragalar component that is engaging the upper face of the astragalus, and wherein the second end of the astragalocalcanean rod both approximates and engages the lower face of the calcaneus so as to progressively compress the calcaneus against the astragalus as the rod advances into the calcaneus from its lower face, resulting in an arthrodesis between the calcaneus and the astragalus.

2. The prosthetic assembly of claim 1 wherein the astragalocalcanean rod comprises a length corresponding to a distance between the upper face of the astragalus and the lower face of the calcaneus.

3. The prosthetic assembly of claim 1 wherein the second end of the astragalocalcanean rod comprises a plurality of threads configured to engage with the calcaneus when coupling the first end of the astragalocalcanean rod to the astragalar component.

4. The prosthetic assembly of claim 1, wherein the second end of the astragalocalcanean rod comprises a ring adapted to press against the lower face of the calcaneus so as to approximate and thereby compress the calcaneus against the astragalus when coupling the first end of the astragalocalcanean rod to the astragalar component.

5. The prosthetic assembly of claim 4, wherein the ring is fixedly secured to the second end of the astragalocalcanean rod.

6. The prosthetic assembly of claim 5, wherein the ring is integral with the second end of the astragalocalcanean rod.

7. The prosthetic assembly of claim 4, wherein the ring moveably surrounds the second end of the astragalocalcanean rod.

8. The prosthetic assembly of claim 1 wherein the first and second ends of the astragalocalcanean rod are linked to each other by a smooth intermediate part and wherein the second end of the astragalocalcanean rod comprises a diameter greater than a diameter of the intermediate part.

9. The prosthetic assembly of claim 1 wherein the lower surface of the astragalar component comprises threads complementary with threads on the first end of the astragalocalcanean rod for coupling by screwing the first end of the astragalocalcanean rod to the lower surface of the astragalar component.

10. The prosthetic assembly of claim 1 wherein the lower surface of the astragalar component comprises an anchor structure for osseous anchoring in the astragalus.

11. The prosthetic assembly of claim 1 wherein the lower surface of the astragalar component comprises an anchor structure for osseous anchoring in the astragalus and internal threads complementary to threads on the first end of the astragalocalcanean rod for coupling by screwing the first end of the astragalocalcanean rod to the lower surface of the astragalar component.

12. The prosthetic assembly of claim 1 wherein the second end of the astragalocalcanean rod is configured to receive a driving tool.

13. The prosthetic assembly of claim 1 wherein the astragalocalcanean rod is adapted to be removed from the ankle after fusion of the astragalus with the calcaneus.

14. The prosthetic assembly of claim 1, further comprising:
   a tibial component of the ankle joint prosthesis adapted for fixation to a distal end of the tibia; and
   a prosthetic bearing shaped to be interposed between the astragalar component and the tibial component.

15. The prosthetic assembly of claim 14 wherein the prosthetic bearing comprises one of a fixed bearing or a moveable bearing.

16. The prosthetic assembly of claim 1, wherein the second end of the astragalocalcanean rod includes a means for engaging the calcaneus.

17. The prosthetic assembly of claim 1, wherein the astragalar component includes a hollow bone-anchoring stub that extends downward from the lower surface.

18. The prosthetic assembly of claim 1, wherein the second end of astragalocalcanean rod includes a recess aligned with a longitudinal axis of the astragalocalcanean rod.

19. The prosthetic assembly of claim 18, wherein the recess has a transverse profile adapted to cooperate with a tool for driving the astragalocalcanean rod in rotation about the longitudinal axis.

20. The prosthetic assembly of claim 1, wherein the astragalocalcanean rod includes an externally smooth middle section located between the first end and the second end.

21. A prosthetic ankle assembly comprising:
an astragalar component comprising an upper articular surface that forms part of an ankle joint prosthesis and a lower surface comprising an anchor structure for osseous anchoring in an astragalus; and
an astragalocalcanean rod sized to be positioned in a bore extending through the astragalus and a calcaneus of an ankle via a lower face of the calcaneus, the astragalocalcanean rod comprising a first end which comprises threads complementary with threads on the astragalar component for coupling by screwing the first end of the astragalocalcanean rod to the lower surface of the astragalar component, and a second end adapted to engage with the lower face of the calcaneus, such that when progressively screwing the first end of the astragalocalcanean rod into the lower surface of the astragalar component, the astragalocalcanean rod is fixed to the astragalar component resting on the astragalus, wherein the second end of the astragalocalcanean rod both approximates and engages the lower region of the calcaneus so as to progressivel compress the calcaneus against the astragalus resulting in an arthrodesis between the calcaneus and the astragalus.

22. A prosthetic ankle kit comprising:
an astragalar component comprising an upper articular surface that forms part of an ankle joint prosthesis and a lower surface comprising a shape adapted to engage an upper face of an astragalus;
an astragalocalcanean rod sized to be positioned in a bore extending through the astragalus and a calcaneus of an ankle via a lower face of the calcaneus, the astragalocalcanean rod comprising a first end adapted to couple to the lower surface of the astragalar component and a second end adapted to engage with the lower face of the calcaneus, such that when progressively coupling the first end of the astragalocalcanean rod to the lower surface of the astragalar component, the astragalocalcanean rod is fixed to the astragalar component resting on the astragalus, wherein the second end of the astragalocalcanean rod both approximates and engages the lower region of the calcaneus so as to progressively compress the calcaneus against the astragalus resulting in an arthrodesis between the calcaneus and the astragalus;
a tibial component of the ankle joint prosthesis adapted for fixation to a distal end of the tibia; and
a prosthetic bearing shaped to be interposed between the astragalar component and the tibial component.

23. A prosthetic ankle assembly comprising:
an astragalar component comprising an upper articular surface that forms part of an ankle joint prosthesis, and a lower surface comprising a hollow bone anchoring stub configured to engage an upper face of an astragalus, wherein the hollow bone anchoring stub includes an internally threaded recess; and
an astragalocalcanean rod adapted to be positioned in a bore extending entirely through the astragalus and a calcaneus of an ankle via a lower face of the calcaneus, the astragalocalcanean rod comprising a first threaded end, which couples by screwing to the internally threaded recess, and a second threaded end adapted to engage with the lower face of the calcaneus, such that when progressively screwing the first threaded end into the internally threaded recess, the astragalocalcanean rod is fixed to the astragalar component resting on the astragalus, wherein the second end of the astragalocalcanean rod both approximates and engages the lower region of the calcaneus so as to progressively compress the calcaneus against the astragalus, resulting in an arthrodesis between the calcaneus and the astragalus.

24. The prosthetic assembly of claim 23, wherein the internally threaded recess is aligned with a longitudinal axis of the hollow bone anchoring stub.

25. The prosthetic assembly of claim 23, wherein the astragalocalcanean rod includes an externally smooth middle section located between the first threaded end and the second threaded end.

26. The prosthetic assembly of claim 23, wherein the lower surface of the astragalar component comprises an arched profile.

* * * * *